United States Patent [19]

Major

[11] Patent Number: 4,707,448

[45] Date of Patent: Nov. 17, 1987

[54] IMMORTAL LINE OF HUMAN FETAL GLIAL CELLS

[75] Inventor: Eugene O. Major, Reston, Va.

[73] Assignee: The United States of America as represented by the Department of Health and Human Services, Washington, D.C.

[21] Appl. No.: 657,630

[22] Filed: Oct. 4, 1984

[51] Int. Cl.$^4$ .................. C12N 5/00; C12N 15/00; C12R 1/91

[52] U.S. Cl. .................. 435/240.25; 435/172.3; 435/948; 435/240.26; 935/57; 935/71

[58] Field of Search ............... 435/235, 236, 237, 240, 435/948, 172.3; 935/57, 71

[56] References Cited

PUBLICATIONS

Brooks, S. E., Amsterdam, D., Hoffman, L. M., Adachi, M. and Scheck, L. "Cytology, Growth Characteristics . . ." *Biological Abstracts* 69:4077 (1979).

Hoffman, L. M., Brooks, S. E., and Schneck, L., "Human Fetal Brain Cells in Culture" *Biochim Biophys Acta* 665:359-361 (1981).

Gluzman, Y. "SV40-Transformed Simian Cells Support the Replication of Early SV40 Mutants" *Cell* 23:175-182 (1981).

Wroblewska, Z., Wellish, M. and Gilden, D., "Growth of JC Virus in Adult Human Brain Cell Cultures," *Biological Abstracts* 71:7071 (1981).

B. Lewin *Genes* John Wiley & Sons, New York, 1983, p. 684.

Brooks, S. E., D. Amsterdam, L. M. Hoffman, M. Adachi and B. Schneck *Journal of Cell Science* 38:211-223, 1979.

Major, E. O., A. E. Miller, P. Mourrain, R. G. Traub, E. DeWidt and J. Sever, *Proc. Natl. Acad. Sci. U.S.A.* 82:1257-1261, 1985.

Eugene Major, SV40, Polyoma and Adenoviruses; Aug. 15-19 1984; p. 160 (abstract of papers presented in 84 Tumor Virus Meeting).

Major et al., JC Virus-Induced Owl Monkey Gliblastoma Cells in Culture . . . ; 1984; pp. 359-367; Virology 136.

Major et al., Human Embryonic Kidney Cells: Stable Transfusion with an Origin-Defective Simian Virus 40 . . . ; Mol & Cell Bio, 1984, pp. 379-382.

*Primary Examiner*—Thomas G. Wiseman
*Assistant Examiner*—Karen Maurey
*Attorney, Agent, or Firm*—Holman & Stern

[57] ABSTRACT

The present invention discloses permanent establishment of an immortal line of fetal glial cells. The fetal glial cell line is capable of mitotically proliferating and continually growing in vitro under suitable culture media and environmental conditions. A method of producing immortalized human fetal glial cell line is also disclosed. The method comprises transfecting primary human fetal glial cells with an origin-defective mutant of SV40 virus, passaging the resulting astroglial cells through suitable number of cycles and obtaining the desired cell line. The cell line of the present invention is capable of supporting multiplication of JC virus.

6 Claims, 17 Drawing Figures

IMMORTAL LINE OF HUMAN FETAL GLIAL CELLS

BACKGROUND OF THE INVENTION

1. Technical Field

The present invention is directed to permanent establishment of an immortal line of human fetal glial cells, more particularly of glial cells which inter alia, support JC virus multiplication.

2. Description of the Prior Art

Glial cells derived from a normal, human fetal brain have a very limited life span once placed in cell culture for laboratory investigation.

There are several examples of normal fetal glial cells established in culture derived from experimental laboratory animals such as the rat (Shipiro, 1983, *Nature* 241: 203–204 and chickens (Giott et al, 1983, in "Neurosciences: Approaches and Tissue Culture", pages 203–225 Ed. Steven Pfeiffer, C.R.C. Press, Boca Raton, Fla.). There are also several human cell cultures which are able to propagate indefinitely in cell culture as cited by Maranda et al 1983 *Proc. Natl. Acad. Sci. USA* 80, 6581–6585. However, in each of these cases, there are serious limitations. In the case of the fetal rat brain, for example, the cells are, obviously, not of human origin eliminating their use as hosts for human viral pathogens restricted for growth to human cells and also, for the same reason, may not serve as good models for basic research experiments on human brain cells. Human brain cells which grow in culture have been derived from adult brain. These cells were neither fetal in their stage of development nor normal since they were derived from cases of multiple sclerosis, or Creutzfeldt-Jacob brain specimens as described by Santoli et al, 1975, *J. Comp. Neurol.* 161, 317–328. There is one report of human fetal glial cells transformed to grow rapidly in culture using infectious SV40 virus as described by Schein 1967, *Neuropathol. Exp. Neurol.* 26, 60–76. Although these cells were not tumorigenic, they gradually died out during cultivation due to cytolytic effects of SV40 virus production. Further, these cells were also not as sensitive to other human viral pathogens as human cells already available for use.

SUMMARY

It is, therefore, an object of the present invention to produce a normal, human glial cell that has an unlimited life span in culture demonstrated by its ability to multiply rapidly and be propagated continually using routine cell culture techniques.

It is a further object of the present invention to produce a cell line which can be used in experiments which require large numbers of homogenous (identical or cloned) cells such as for examining the physiology and metabolism of human glial cells.

It is yet another object of the present invention to produce a glial cell line which can be used as a host substrate for the multiplication of human viral pathogens which are neurotropic.

It is a still further object of the present invention to produce a cell line which can be used to reproduce recombinant DNA molecules (e.g., human or viral genes) that contain the DNA origin of replication of the simian virus SV40 in a plasmid vector.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 2-A to 2-D show results of in situ hybridization of JCV infected PHFG cells (2A,2B) and SVG cells (2C,2D) with a JCV biotin labeled DNA probe (2A,2C) or a control with no probe DNA (2B,2D). Darkly stained nuclei result from biotin-avidin-peroxidase complex reacting with biotin labeled DNA in the presence of $H_2O_2$ and diaminobenzidene;

DETAILED DESCRIPTION OF THE INVENTION

Figures 1, 1B:
FIGS. 1-1A to 1-1D and 1-2E to 1-2H show identification of cell types in cultures of PHFG (1-1A to 1-1D) and SVG (1-2E to 1-2H). Photographs show: (1-1A, 1-2E) representative field of cells in phase contrast, bright field, (1-1B, 1-2F) use of mouse anti-gal c antibody and rhodamine conjugated goat anti-mouse antibody to detect oligodendroglial cells, (1-1C,1-2G) use of mouse anti-GFAP antibody and fluorescein conjugated goat anti-mouse antibody to detect astroglial cells, (1-1D,1-2H) use of hamster anti SV40 T protein and fluorescein conjugated, goat anti-hamster antibody. Note that cells in 1-1A, 1-1B and 1-1C are identical having been treated with anti-gal c and subsequently, anti-GFAP antibodies and photographed using screening titers for either rhodamine (gal c) or fluorescein (GFAP)

These and other objects of the present invention are achieved by an immortal line of human fetal glial cells. The cells of the present invention are capable of mitotically proliferating ard continually growing in vitro under suitable culture media and environmental conditions. Addtionally, these cells are capable of supporting at least JC virus multiplication. A deposit of said line of human fetal glial cell having the properties as described herein has been made with the American Type Culture Collection, Rockville, Md., and is assigned the accession number ATCC CRL 8621.

The permanent line of human glial cells of the present invention results from the unexpected finding that an origin-defective-mutant (ori⁻) of SV40 virus is able to immortalize human fetal glial cells. These cells, which are hereinafter designated SVG, provide rapidly growing cultures of human astroglial cells which are capable of reproducing infectious JC virus following infection or transfection in concentrations and at the same rate as primary human fetal glial cells. The SVG cell line also produces an SV40 T protein which recognizes the SV40 origin of replication in the plasmid vector, pSV$_2$. One of the advantages of the SVG cell line of the present invention is its unique ability to act as a host for a human papovavirus, JCV, and makes the production of large numbers of homogenous astroglial cells possible for molecular and biological studies of human fetal brain.

Preferred methods and materials employed in the practice of the present invention are now described, although other suitable methods and materials could also be advantageously applied. All publications or references mentioned hereunder are incorporated herein by reference.

MATERIALS AND METHODS

Cell Cutures. Human fetal brain material is dissected from 8–12 week old abortuses, aspirated through a 19 guage needle, washed twice in Eagle's minimum essential medium (E-MEM) obtained from Gibco, N.Y., and planted into 25 cm$^2$ tissue culture flasks pretreated with poly-D-lysine (0.1 mg/ml for 5 mins). The cultures are grown and maintained on E-MEM supplemented with 20% fetal bovine serum, 75 µg/ml streptomycin and 75 units/ml penicillin, 1% dextrose (vol/vol) and 2 µg/ml fungizone (Gibco). Whether the cultures are treated with virus or viral DNA, the same medium formulation is used. Incubation of the cultures is done at 37° C. in a 5% CO$_2$, humidified environment.

Virus and DNA Preparations. The Mad-1 strain of the human papovavirus JCV is acquired from the American Type Culture Collection as a lyophilized stock. Growth of the virus is preliminarily done in primary human fetal glial (PHFG) cultures. Virion production is assayed by hemaggulutination of human type O erythrocytes at 4° C. using the standard microtiter system. JCV genomic DNA is prepared from the plasmid pJC as described by Miller et al, 1983, in *Polyomaviruses and Human Neurological Diseases*. Ed. Alan R. Liss, 29–40. JCV DNA is purified from the pBR322 vector following Bam H1 and Hha 1 endonuclease (BRL) digestion and passage over a Sephacryl column S-1000 (Pharmacia). The pSV$_2$ vector is obtained from Bethesda Research Laboratories (BRL), Bethesda, Md. The pSV$_2$-JC recombinant plasmid is constructed using conventional recombinant DNA techniques conforming to the current NIH guidelines. The origin defective mutant of SV40 (1-11) was provided by Y. Gluzman, Cold Spring Harbor Lab, N.Y., as an insert in the pMk16 vector at the Bam H1 site. This mutant DNA has a 56 base pair (bp) deletion at the Bg 1 site of the SV40 DNA replication region. All plasmids are grown in *E coli* K-12 hosts, HB101 or C600, amplified using chloramphenicol and purified by a cleared lysis method as described by Clewell, 1972, *J. Bacteriol.* 110, 667–676. Plasmid DNAs are isolated as form I molecules following centrifugation in cesium chloride, ethidium-bromide equilibrum gradients as described by Radloff et al, 1967, *Proc. Natl. Acad. Sci. USA* 57, 1514–1521.

Biotin Labeling of JC Viral DNA. JCV genomic DNA is purified as described above and labeled with biotinylated dUTP by nick translation procedures described by Birgati et al. 1983 *Virol.* 126, 32–50. Reagents for the nick translation procotol are obtained from ENZO Biochemicals, New York . Trace amounts of $^3$H-dATP are used during incorporation to follow the efficiency of the nick translation. The JC DNA probe contains approximately 28% substitution of dTTP with biotin-dUTP. The JC-biotinylated probe is separated from unincorporated nucleotide triphosphates using a 1.0 ml column of Sephadex G50 packed into a tuberculin syringe and centrifugated at 400 rpm (120 g) for 2 min. Size of the probe is estimated at 80–300 base pairs by electrophoresis through a 1.4% agarose gel in TBE buffer (89 mM Tris, pH 98.0; 89 mM boric acid, 25 mM EDTA) in direct comparison with the 123 nucleotide base pair sizing ladder sequences purchased from BRL. Probe concentration is adjusted to 20 ng/µl.

In situ DNA-DNA Hybridization. Cells which would undergo a hybridization are planted directly onto glass coverslips pretreated with poly-D-lysine and placed in 15 cm$^2$ cluster dishes (Costa Cambridge, Massachusetts). Virus infection or DNA transfection is done on cells after establishment of growth on the coverslips. After appropriate time, the coverslips are removed and fixed in 4% paraformaldehyde in PBS (phosphate buffered saline, pH 7.4 containing 6.7 mM NaH$_2$PO$_4$, and 0.85% NaCl) for 25 minutes at room temperature, washed once in PBS and dehydrated in graded ethanol concentrations. Coverslips can be stored dessicated at 4° C. for several months. The in situ hybridization protocol followed the outline of Brigati et al, supra, with certain modifications. Coverslips are attached to microscope slides using epoxy, washed in PBS, treated with 0.1N HCl for 10 min. 0.01% Triton X-100, rinsed in PBS, and digested with 300 ng/ml protease (Boeringer-Mannheim) for 10 min. Protease concentration is critical and assayed carefully for individual lots which gave the best results. Following protease treatment, the coverslips are rinsed 3 times in PBS-glycine and refixed in 4% paraformaldehyde before dehydration in graded ethanol concentrations. The hybridization reaction mixture routinely contains 50% (vol/vol) deionized formamide, 10% dextran sulfate, 400 µg/ml herring sperm DNA, and 20 µg/ml biotinylated probe DNA in 0.3M NaCl and 0.03M Na citrate. Twenty microliters of the hybridization mixture is applied per coverslip. A larger coverslip is placed on top and sealed by rubber cement. The cells and probe DNA are denatured together in an oven set for 80° C. for 15 min., cooled quickly to room temperature and placed at 37° C. for 36 hr. Detection of the hybridization signal is made using the avidin-biotin-peroxidase complex (ENZO Biochemicals, New York) as described by Hsu et al. 1981, *J. Histochem. Cytochem.* 29, 577–580.

Fluorescent Antibody Assays for SV40 T Protein and Glial Cell Markers. Cells to be tested for the nuclear SV40 T protein and glial fibrillary acidic protein (GFAP) are fixed on coverslips using acetone-methanol treatment at −20° C. for 10 min. Cells designated for GFAP staining are also fixed with 4% paraformaldehyde in PBS for 5 min. at room temperature and methanol for 5 min. at room temperature to permeablize the cell's membrane. Fluorescein or rhodamine conjugated antibodies are obtained from Cappel Laboratories, Westchester, Pa. The anti-SV40 T antiserum is derived from a tumor bearing hamster as described by Major et al, 1984, *Virology:* 136, 359–367 The anti GFAP antibody is obtained from Lab Systems (Helsinki, Finland) as a mouse monoclonal antibody made against the human GFAP of an astrocytoma. The mouse antigalactocerebroside, gal C, was a gift from D. van Alstyne, Dept. of Medicine, University of British Columbia, Vancouver, Canada. Cells to be tested with anti gal C antibody are harvested live from culture, washed in E-MEM and HEPES buffer (catalog #H3375, Sigma Chem. Co., St. Louis, Mo.) and reacted with sera in microfuge tubes. This procedure greatly enhances the ability of oligodendroglial cells to react with the gal C antibody. All microscopic examinations are done using a Leitz Vario-Orthomat equiluminescent microscope using a mercury lamp for fluorescence tests.

Development of SV40 Transformed Human Glial Cells. As has been mentioned herein supra, primary human fetal brain tissue between 8-12 weeks gestation can be dispersed and planted into cell cultures which produce mainly spongioblast and glial cells as described by Shein, 1965 *Exp. Cell Res.* 40, 554-569. It should be noted that if these cultures are refed at weekly intervals, the brain cells will survive for several months but show little cell proliferation. Since glial cells do have mitotic capability, the Applicant conceived and made it possible to extend the life span and growth of glial cells in culture by inducing cell division in the glial cells by transfecting the cells with a mutant of SV40 DNA. This DNA is itself unable to multiply due to a deletion in its origin of replication (ori$^-$) but is able to transform cells to unlimited growth potential as described by Gluzman, 1981, *Cell,* 23, 175-182. PHFG cultures are grown in 25 cm$^2$ flasks for 3 weeks. After this time, they are transfected with 100 μg/flask of plamid DNA (pMK16) containing the SV40 ori$^-$mutant 1-11 using the calcium phosphate precipitation technique as described by Graham et al 1973, *Virol.* 52, 456-467. For the first 3-4 weeks the cultures appear normal but require weekly refeeding. After this time, proliferation of glial cells in separate areas of the flasks is evident. At this time the cells are transferred by trypsinization (0.025%) to new cultures at a 1:2 ratio and designated SVG. Fluorescence antibody assays to detect the SV40 T protein using a hamster tumor bearing serum to SV40 T protein demonstrates that only 10% of cells are positive. The cultures are passed every 10 days before any increase in the number of T protein positive cells is detected. By 14 weeks or sixth passage up to 25th passage, 100% of cells in all cultures show nuclear staining with the anti SV40 T protein antibody. Radioimmune precipitation assay also identifies the 94K dal SV40 T protein resolved on polyacrylamide gels. Table 1 lists the biological properties of the SVG cell line which have been consistent for all passages tested.

TABLE 1

| Biological Characteristics of the SVG Cell Line | | | | |
|---|---|---|---|---|
| Cell Type | Anchorage independent growth | Saturation density/cm$^2$ | Passage in culture | T Protein in cell nucleus |
| Primary human fetal glial | (—) | 1 × 10$^4$ | Limited | <0.001% |
| SVG | (—) | 2 × 10$^5$ | Continuous | 100% |

The SVGF cells display the phenotypes of a continuous cell line because they grow to a very high saturation density with a 18 hr generation time. They do not show the transformed phenotype of anchorage independent growth, however, which is characteristic of SV40 transformed cells. The cell morphology is also not altered during the course of establishment of the cell line. A dense piling up or foci of cells formed is also not detected. There is a transition from non-homogeneity of cell types including astrocytes, oligodendrocytes, and fibroblast type cells into a homogenous cell morphology more typical of the astroglial cell.

Identification of SVG Cells as Atroglial. Characteristically, astroglial cells can be recognized by the presence of an intermediate filament composed of glial fibrillary acidic protein, GFAP. Oligodendroglial cells, on the other hand, are myelin producing cells and can be identified by their synthesis of a galactocerebroside, gal C, which is a component of myelin. Therefore, the SVG cells were tested in comparison to PHFG cells for the presence of the neural cell markers.

Figures 1, 1D:
Figures 1, 1A:
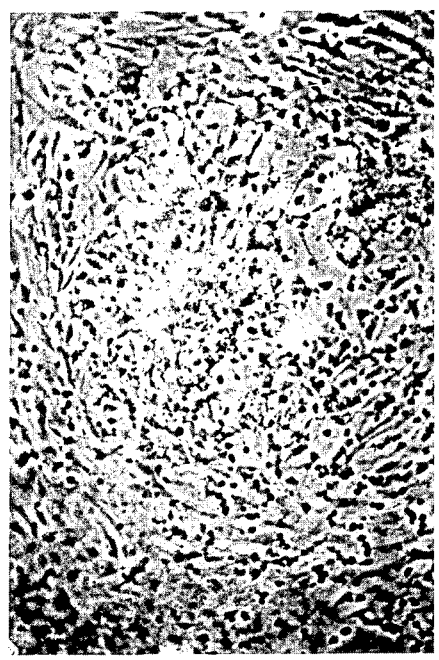
Figures 1, 1C:
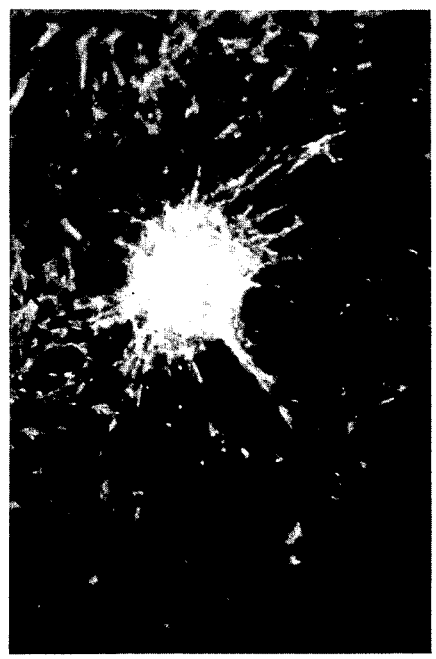

FIGS. 1-1A to 1-1D are photomicrographs of normal PHFG cells showing: (FIGS. 1-1A) oligodendroglial cells which grow in clumps and send out thin processes and astroglial cells which surround the oligodendroglial cells and can be recognized by their larger nucleus; (FIGS. 1-1B) reactivity of the identical culture shown in FIGS. 1-1A to antibody to gal C detecting only the cells in the dense clumped area; (FIGS. 1-1C) reactivity of the same culture shown in FIGS. 1-1A with antibody to GFAP detecting the astroglial cells present surrounding the oligodendroglial cells; and (FIGS. 1-1D) no reactivity of PHFG cells to antibody to SV40 T protein.

Figures 1, 2, 2F:
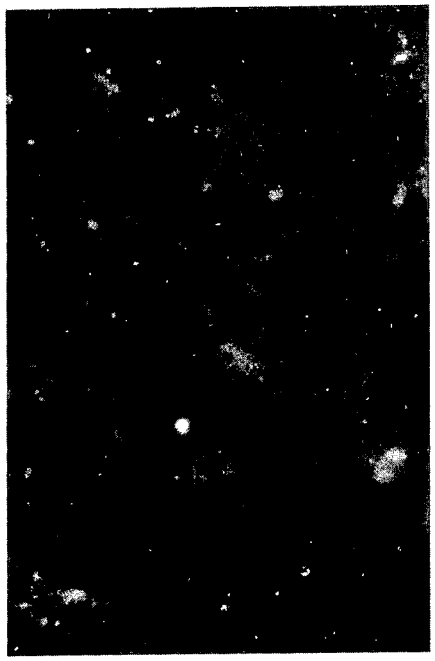
Figures 1, 2, 2H:
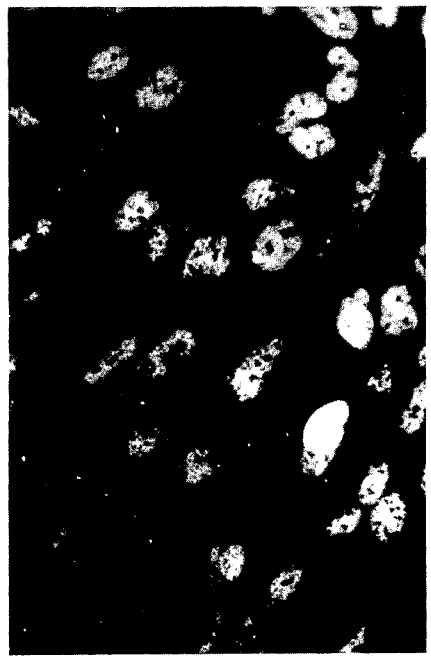
Figures 1, 2, 2E:
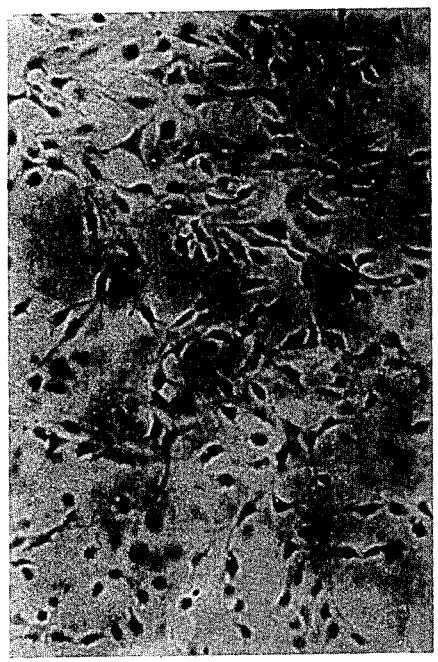
Figures 1, 2, 2G:
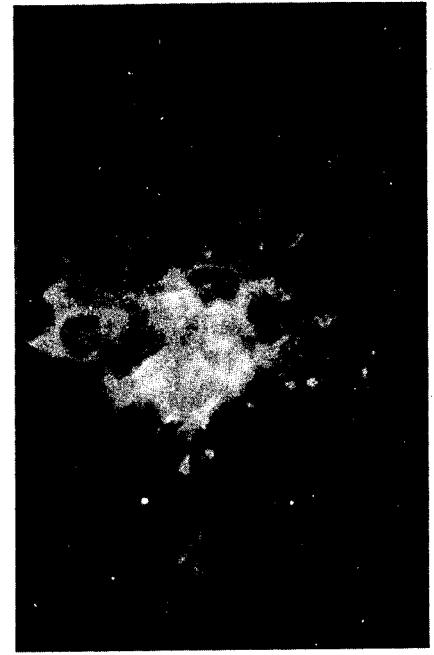
Figure 2B:
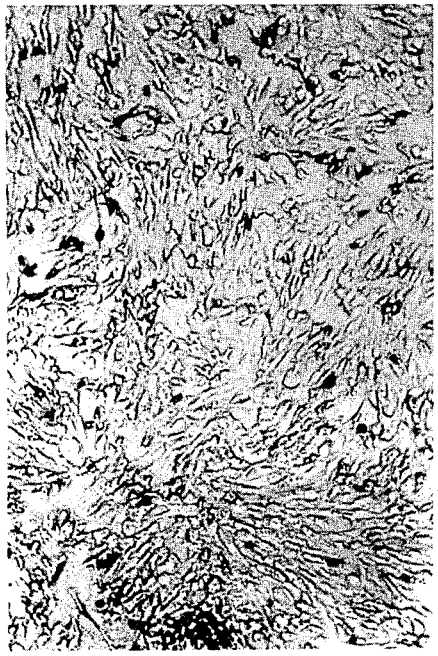
Figure 2D:
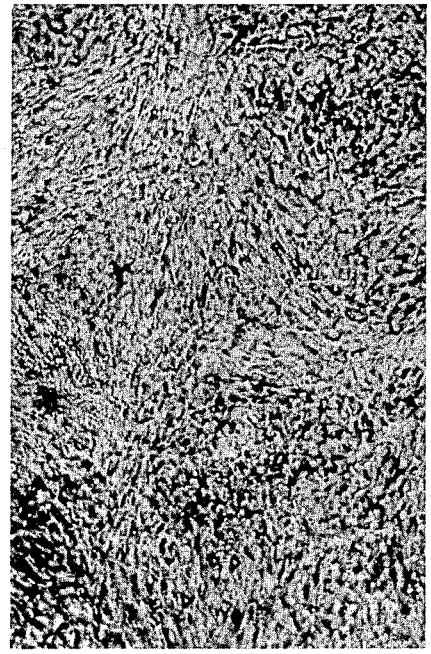
Figure 2A:
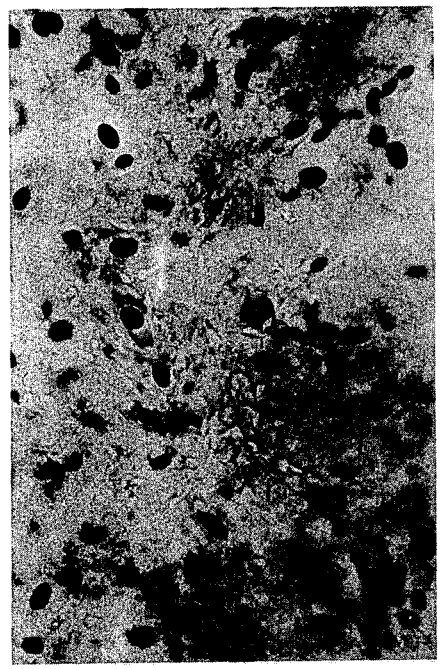
Figure 2C:

FIGS. 1-2E to 1-2H are photomicrgraphs of SVG cells at their 15th passage showing: FIGS. 1-2E a homogenous morphology of cells similar to astroglial cells; FIGS. 1-2F no reactivity to anti gal C antibody; FIGS. 1-2G reactivity to anti GFAP antibody which stains the cytoplasm in a pattern similar to the staining of SVG cells for actin fibers as typical of transformed cells; FIGS. 1-2H 100% of cells reacting to anti SV40 T protein antibody, Schein, 1967, *Neuropathol. Exp. Neurol.* 26, 60-76. had used SV40 virus to infect human fetal neuroglial cells and found that SV40 was cytolytic for glial precursor or spongioblast cells but did' transform astrocytes. The Applicant has now produced for the first time a human fetal glial cell line using the ori$^{-}$ mutant of SV40 which does not induce cytolysis in glial cells.

Multiplication of JCV in SVG Cells. To assess whether SVG cells could support JCV multiplication in direct comparison with PHFG cells, the following test is conducted. Human fetal brain tissue is uniformly distributed onto coverslips in multiple 15 cm$^2$ cluster dishes and allowed to establish almost confluent cultures of glial cells. SVG cells are plated into cluster dishes at low density so that the time in culture before virus absorption is similar to that of human fetal glial cells. 160 HA units of JCV Mad-1 strain are inoculated equally into each of 6 wells per cluster plate of SVG or PHFG cells. One week, two weeks, and three weeks after viral absorption, coverslips are removed and fixed appropriately or cells are harvested for virus assays to examine the rate of JCV T protein synthesis, DNA replication, and the amount of virus produced. Table 2 lists the data from such a test.

TABLE 2

| Kinetic Study of JCV Multiplication in SVG Cells and PHFG Cells | | | | | | | | |
|---|---|---|---|---|---|---|---|---|
| | 7 days[a] | | | 14 days | | | 21 days | | |
| | T[b] protein | DNA[c] | Virions[d] | T protein | DNA | Virions | T protein | DNA | Virions |
| PHFG | 70% | 6.2% | 20 | 50% | 9.2% | 640 | 15% | 35% | 10,240 |

TABLE 2-continued

Kinetic Study of JCV Multiplication in SVG Cells and PHFG Cells

| | 7 days[a] | | | 14 days | | | 21 days | | |
|---|---|---|---|---|---|---|---|---|---|
| | T[b] protein | DNA[c] | Virions[d] | T protein | DNA | Virions | T protein | DNA | Virions |
| SVG | NA[e] | 4.8% | ~10 | N/A | 33% | 320 | NA | 53% | 5,120 |

[a] Time period following virus adsorption.
[b] T protein determined as percent of cells staining by immunofluorescence assay.
[c] DNA replication determined as percent of cells hybridizing to biotin labeled JC DNA probe.
[d] Virions detected by hemagglutination of human type O erythrocytes by infected cells harvested from the cell culture medium.
[e] Not applicable.

It should be noted that synthesis of the JCV T protein cannot be evaluated in SVG cells because both JCV T and SV40 T proteins antigenically cross react. The only available monoclonal antibody to JCV T protein is pAb108 developed and supplied by E. Gurney, Dept. of Microbiology, University of Utah Medical Center, Salt Lake City, for SV40 T protein which is found to cross react with the JCV T protein as described in Major et al., 1984, *Virol.* 136, 359–367. Since SVG cells constitutively produce SV40 T protein, its synthesis from that of JCV cannot be distinguished.

In the PHFG cells, JCV T protein is detected in the majority of cells, 70% and 50%, in the first two weeks. Since oligodendroglial cells do not compose more than half of the cells in these cultures as determined by microscopic observations of cell morphology, JCV clearly has the ability to infect astroglial cells. By the end of the third week of infection, cells producing T protein are reduced to 15%, probably reflecting loss of infected cells to cytolysis due to JC virus production. The reduction of cells with detectable T protein may also reflect the autoregulation of T protein synthesis.

Viral DNA replication is assayed by in situ DNA-DNA hybridization of infected cells with a biotin labeled JC DNA probe. This technique was preferred since it allows to quantitate the percent of cells replicating JC DNA while maintaining the morphology of oligodendroglial and astroglial cells. This non-radioosotope technique is clearly less sensitive in detecting low copy numbers of viral DNA but is superior to the use of isotopically labeled probes in the preservation of cell structure as demonstrated by Singer et al, 1982, *Proc. Natl. Acad. Sci.* 79, 7331,7335. For example, viral DNA integrated in only a few copy in the cell chromosome cannot be detected using biotin labeled DNA probes. Viral DNA, however, generated during replication exists in high copy number and can be readily detected with a high degree of specificity using a biotin labeled DNA probe as described in Brigati et al, 1983, *Virol.* 126, 32–50. In the present tests, several biotin labeled JCV DNA probes did not detect JCV DNA sequences integrated in a JC virus induced monkey glioblastoma cell line as described in Major et al, 1984, *Virol.* 136, 359–367, nor could these probes detect SV40 DNA sequences in either SVG or SV1 cells even though JCV DNA cross hybridizes to SV40 DNA as demonstrated by more sensitive techniques in Law et al, 1979, *Virol.* 96: 576–587. The same DNA probes could detect JCV DNA sequences if they were in high copy number as a result of replication in PHFG and SVG cells as demonstrated by the data summarized in Table 2 and shown in FIGS. 2A to 2D. This allows to accurately assess the percent of cells replicating JCV DNA in infected PHFG and SVG cells. PHFG cultures showed 6.2% of cells synthesizing viral DNA during the first two weeks of infection. Between the second and third weeks, at the time when few cells are synthesizing T protein, there is a 4 fold increase in the number of cells replicating JC DNA in SVG cells, the increase in the number of cells hybridizing to JC DNA probe between the first and second weeks is 7 fold and between second and third weeks is 1.6 fold. The striking difference between JCV DNA synthesis in PHFG cells and SVG cells is at the end of the second week at which time only 9.2% of PHFG cells compared to 33% of SVG cells hybridize to JC DNA probe (FIGS. 2A to 2D).

Viron production is measured by hemagglutination of human type O erythrocytes. Interestingly, approximately equal amount of JC virus is produced in both cell types and at the same rate, a 32 fold increase between the first and second weeks and a 16 fold increase between the second and third weeks. Infectious JC virus is recovered from both cell types which grow in cultures of either PHFG or SVG cells.

Figure 3:
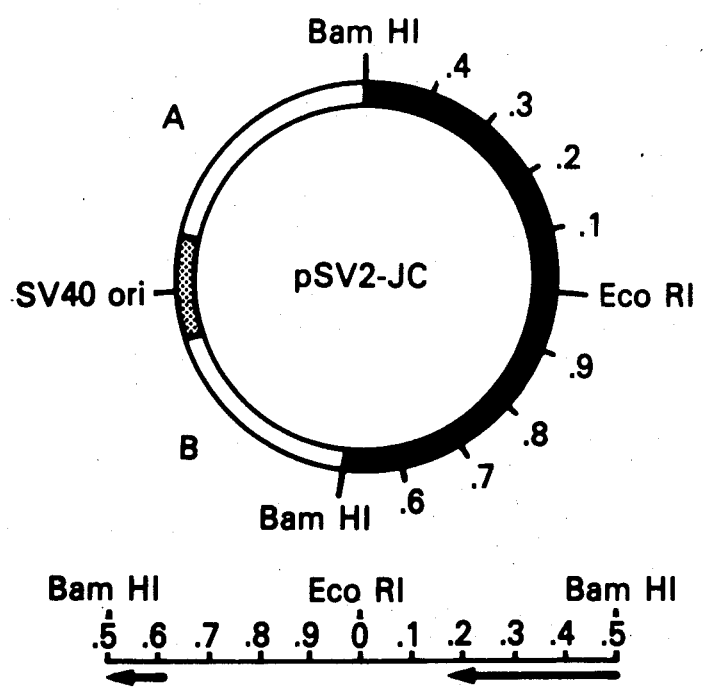
FIG. 3. represents an schematic of the circular pSV2-JC plasmid. The heavy line represents the JCV genome in the plasmid and in its linear form cut at the Bam H1 site. The direction of trascription of the JCV T protein (from approximately 0.62 to 0.18 map units) is indicated by the arrow. A represents sequences from pBR322 and B represents Eco gpt and SV40 polyadenylation sequences.
Figure 4B:
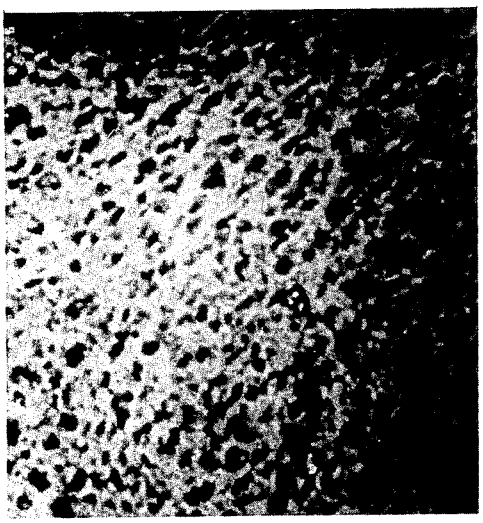
FIGS. 4A to 4D show the results of in situ hybridization of SVG cells (4A,4B) and SV1 cells (4C,4D) with a biotin labeled JCV DNA probe at 16 hrs (4A,4C) and 110 hrs. (4B,4D) following transfection with the pSV2-JC plasmid DNA. Detection of hybridization signal is the same as in FIGS. 2A to 2D.
Figure 4D:
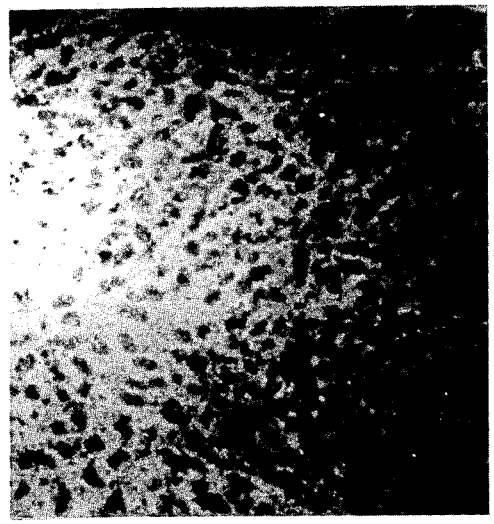
Figure 4A:
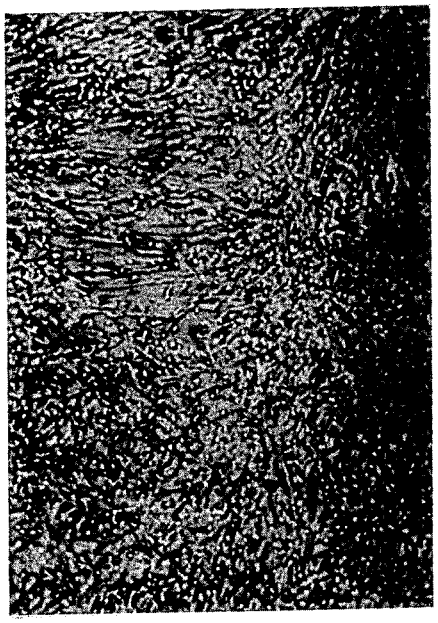
Figure 4C:
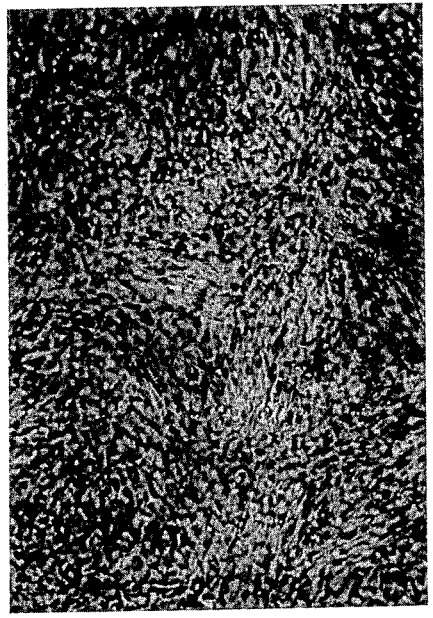

SVG T Protein and DNA Replication. To test the ability of the T protein made in SVG cells to replicate SV40 origin containing sequences, the JCV DNA genome was inserted at the Bam H1 site in the pSV$_2$ vector (FIG. 3). Bam H1 endonuclease cleaves JCV DNA in the middle of its early region thus inactivating synthesis of a functional JCV T protein. 15 $\mu$g of pSV$_2$-JC recombinant molecules are transfected into SVG cells and SV1 cells, a similarly constructed cell line produced from human embryonic kidney as described in Major et al, 1984, *Mol. Cell Biol.* 4, 379–382. The cells are hybridized to JCV DNA biotin labeled probe at 16 hrs and 110 hrs after transfection. No hybridization signal is detected at 16 hrs. However, at 110 hrs, presumably after replication is allowed to proceed and accumulate higher copy numbers of JCV DNA, 80% of both cells hybridize to the JCV DNA probe (FIGS. 4A to 4D). Linear JCV DNA which is cleaved at the Bam H1 site is also transfected into SVG and SV1 cells and hybridized to the JCV DNA probe at 110 hrs. No hybridization signal is detected. This experiment indicates that the SV40 T protein synthesized in the SVG cells is able to replicate the pSV2-JC DNA. The hybridization of the cells and the JCV DNA probe could not have resulted from either the input, transfected DNA or JCV DNA replicated by its own T protein synthesis.

It is clear from the above that a unique cell line of human fetal glial cells established by introduction of the ori$^-$mutant of SV40 has been produced. Their growth patterns (Table 1) define the cells as a continuous culture. Their reactivity to anti GFAP antibody and cell morphology (FIGS. 1-1A to 1-1D and 1-2E to 1-2H) identify the cells as astroglial. Since the cells are anchorage dependent, the SVG cells can be considered as immortalized by SV40 and not malignantly transformed. The homogeneous population of SVG cells make them a good source of normal, human fetal astroglial cells for more intense molecular and genetic studies which are not possible with mixed cell cultures derived from normal brain tissue.

In addition to these properties, the data presented in Table 2 and FIGS. 2A to 2D demonstrate that SVG cells are able to support the multiplication of JCV. Interestingly, JCV is produced very slowly in PHFG cultures as described in Martin et al, 1983 *J. Gen Virol.* 64: 2271-2280, requiring weeks of culturing during which time some virus can be harvested from cell culture fluid. The SVG cells, although growing rapidly, do not reduce the length of time JCV requires for multiplication throughout a culture. Infected SVG cells produce JCV at the same rate as the PHFG cells. Since SVG cells are astroglial, however, and JCV is thought to grow only in spongioblasts or oligodendroglial cells, as reported by ZuRhein, 1972: *Path Nurveous System*, McGraw Hill pages 2893-2912 and Norkin, 1982, *Microbiological Reviews* 46, 384-4125, the data from these tests provide direct evidence of JC virion production from astroglial cells.

In summary, some of the distinguishing characteristics of the SVG cells of the present invention may be listed as follows:

a. Presence of Astroglial cells as evidenced by the presence of glial fibrillary acid protein (GFAP) fluorescent staining using monoclonal antibody to GFAP and lack of staining for galactocerebroside which is specific for oligodendroglial cells;

b. Generation time of 18 hrs as judged by growth curve of logarithmically growing cells;

c. High saturation density growth of $1.6 \times 10^5$ cells/cm$^2$ as determined by repeated cell counts;

d. Anchorage dependent for growth by determing whether the cells are able to form colonies in semi solid agar;

e. SV40 T protein positive (100% of cells) by fluorescent staining and immunoprecipitation of the SV40 protein using monoclonal antibody;

f. Capable of replicating plasmid DNA containing the SV40 origin of replication as judged by in situ hybridization; and g. Susceptible to JC virus infection, a human neurotropic virus which causes a fatal demyelinating disease, as judged by multiplication of progeney JC virions following infection of cell cultures. The cells are also susceptible to herpes viruses I and II and cytomegalovirus (CMV).

Of course, much remains to be studied about the relationship between JCV and the cells it infects and the demyelinating disease it causes. However, the establishment of the SVG cell in accordance with the present invention provides a unique tool to conduct such studies on a molecular and biochemical level not limited by the problems which primary brain tissue cultures present. Furthermore, the SVG cells of the present invention allow these cells to be useful as potential eukaryotic vector for replication of foreign genes and as hosts for growth of human viral pathogens which are neurotropic and specifically require brain cells for multiplication and identification.

It is understood that the examples and the embodiments described herein are for illustrative purposes only and that various modifications or changes in light thereof will be suggested to persons skilled in the art and are to be included within the spirit and purview of this application and the scope of the appended claims.

What is claimed is:

1. A continuous and permanently established line of human fetal glial cell being a eucaryotic host for the growth of human viruses and producing homogeneous astroglial cells.

2. The cell line of claim 1 at least supporting multiplication of JC virus.

3. The cell line of claim 1 being ATCC CRL 8621.

4. A method of producing immortalized human fetal glial cell line comprising transfecting primary human fetal glial cells with an origin-defective mutant of SV40 virus, passaging the resulting astroglial cells through sufficient number of cycles to obtain a mitotically proliferating and continually growing fetal glial cells and recovering a continuous and permanently established line of human fetal glial cell for producing homogeneous astroglial cells and acting as eucaryotic host for the growth of human viruses.

5. The method of claim 4 wherein said fetal glial cells support multiplication at least of JC virus.

6. An immortal line of human fetal glial cell being a eucaryotic host produced by the method of claim 4.

* * * * *